US010640692B2

(12) United States Patent
Song et al.

(10) Patent No.: US 10,640,692 B2
(45) Date of Patent: May 5, 2020

(54) GRAPHENE OXIDE-NANODIAMOND COMPOSITE, MANUFACTURING METHOD THEREOF, AND NANOFLUID INCLUDING THE SAME

(71) Applicants: Hyundai Motor Company, Seoul (KR); Kia Motors Corporation, Seoul (KR)

(72) Inventors: Kyong Hwa Song, Seoul (KR); Byung Wook Kim, Gyeonggi-do (KR); Jinwoo Kwak, Gyeongsangbuk-do (KR); Jinhyeok Cha, Gyeonggi-do (KR); In Woong Lyo, Gyeonggi-do (KR); Han Saem Lee, Seoul (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 61 days.

(21) Appl. No.: 15/961,549

(22) Filed: Apr. 24, 2018

(65) Prior Publication Data
US 2018/0237677 A1    Aug. 23, 2018

Related U.S. Application Data

(62) Division of application No. 15/155,239, filed on May 16, 2016, now abandoned.

(30) Foreign Application Priority Data

Feb. 3, 2016    (KR) ........................ 10-2016-0013597

(51) Int. Cl.
*C09K 5/08*    (2006.01)
*C09K 5/10*    (2006.01)
(Continued)

(52) U.S. Cl.
CPC ................ *C09K 5/10* (2013.01); *C01B 32/15* (2017.08); *C01B 32/198* (2017.08); *C01B 32/28* (2017.08); *C07C 45/00* (2013.01); *C07C 51/16* (2013.01)

(58) Field of Classification Search
CPC ............ C09K 5/08; C07C 45/00; C07C 51/16
(Continued)

(56) References Cited

U.S. PATENT DOCUMENTS 8,703,490 B2 *   4/2014   Jackson ................ B82Y 30/00
                                                             252/408.1
9,296,615 B2 *   3/2016   Branson ................ B82Y 30/00
(Continued)

FOREIGN PATENT DOCUMENTS

JP    2007-297261 A    11/2007
JP    2014-172781 A     9/2014
(Continued)

OTHER PUBLICATIONS

Thanh et al. "A few-layer graphene-graphene oxide composite containing nanodiamonds as metal-free catalysts", J. Mater. Chem. A, 2014, 2, 11349. Published Jun. 13, 2014 (Year: 2014).*
(Continued)

*Primary Examiner* — Jane L Stanley
(74) *Attorney, Agent, or Firm* — Mintz Levin Cohn Ferris Glovsky and Popeo, P.C.; Peter F. Corless (57) ABSTRACT

Disclosed herein is a composite comprising a graphene oxide and a nanodiamond that is chemically bonded on a surface of the graphene oxide.

10 Claims, 9 Drawing Sheets

(51) Int. Cl.
  *C01B 32/15* (2017.01)
  *C01B 32/28* (2017.01)
  *C01B 32/198* (2017.01)
  *C07C 51/16* (2006.01)
  *C07C 45/00* (2006.01)

(58) Field of Classification Search
  USPC .......................................................... 252/74
  See application file for complete search history.

(56) References Cited

U.S. PATENT DOCUMENTS

| | | | |
|---|---|---|---|
| 9,598,558 B2* | 3/2017 | Myllymaki | C08K 3/38 |
| 9,987,608 B2* | 6/2018 | Pigos | B01J 13/0095 |
| 10,167,392 B2* | 1/2019 | Suresh | C09D 1/00 |
| 2013/0341028 A1 | 12/2013 | Christian et al. | |

FOREIGN PATENT DOCUMENTS

| | | |
|---|---|---|
| JP | 2015-127364 A | 7/2015 |
| KR | 10-2015-0015245 A | 2/2015 |
| WO | 2009/060613 A1 | 5/2009 |

OTHER PUBLICATIONS

Shenderova et al. "Modification of detonation nanodiamonds by heat treatment in air", Diamond & Related Materials, 15, 2006, 1799-1803; published online Oct. 13, 2006 (Year: 2006).*

Kreuger et al. "Functionality is Key: recent progress in the surface modification of nanodiamond", Advanced Functional Materials, 2012, 22, 890-906. published Mar. 7, 2012 (Year: 2012).*

Kausar, Ayesha, "Formation and Properties of Poly (vinyl butyral-co-vinyl alcohol-co-vinyl acetate) / Polystyrene Composites Reinforced with Graphene Oxide-Nanodiamond", American Journal of Polymer Science, (2014) 4(2): 54-62.

Wang et al. "Nanodiamond particles/reduced graphene oxide composites as efficient supercapacitor electrodes", Carbon, 68, 2014, 175-184. published online Nov. 13, 2013.

Yao et al., "Impedance analysis of quartz crystal microbalance humidity sensors based on nanodiamond/graphene oxide nanocomposite film", Sensors and Actuators B: Chemical, 211, 2015, 52-58, published online Jan. 28, 2015.

Taha-Tijerina et al., "Nanodiamond-based Thermal Fluids", ACS Applied Materials and Interfaces, 6, 2014, 4778-4785, published online Mar. 21, 2014.

* cited by examiner

GRAPHENE OXIDE-NANODIAMOND COMPOSITE, MANUFACTURING METHOD THEREOF, AND NANOFLUID INCLUDING THE SAME

CROSS-REFERENCE TO RELATED APPLICATION

This application is a Divisional of Application 15/155,239, filed on May 16, 2016, which claims priority to and the benefit of Korean Patent Application No. 10-2016-0013597 filed in the Korean Intellectual Property Office on Feb. 3, 2016, the entire contents of which are incorporated herein by reference.

BACKGROUND OF THE INVENTION (a) Field of the Invention

The present invention relates to a composite comprising a graphene oxide and a nanodiamond, a method of manufacturing the same, and a nanofluid including the same.

(b) Description of the Related Art

A nanofluid is a suspension that includes different types of nano-sized materials dispersed therein in order to overcome a limitation of thermal conductivity of a single fluid. The nanofluid includes a solvent and a filler, and water and ethylene glycol which have high thermal conductivity and high temperature stability have been generally used as the solvent. In order to increase thermal conductivity of a fluid, a nanomaterial which has excellent thermal conductivity can be added to the fluid.

Research on the nanofluid used in a cooling field of a vehicle and a cooling field of electronics has been actively performed. For example, nanoparticles have been added to engine antifreeze of the vehicle to produce an engine antifreeze having excellent heat transfer performance, and nanoparticles have been added to a transmission oil for reducing frictional force and for improving heat transfer performance. In the commercialization of a nanofluid of used in the vehicle cooling field, technology for maintaining dispersion and floating characteristics thereof may be essentially required.

Moreover, for a use in the vehicle, a stable material that does react with a material of a pipe where a coolant flows may be selected.

Currently, materials such as metal, ceramic, and carbon have attracted attention as a filler for application of the nanofluid. Although there is no limitation to a shape of the filler, a particle type filler and a fiber type filler have been mainly used for dispersion stability in a solvent. Further, precipitation can be prevented and heat can be effectively transferred in the fluid by manufacturing the filler in a nanosize.

Generally, metal and ceramic materials have high specific gravity, thus they may be precipitated when used for a long period of time. Recently, a carbon nanotube and a carbon material such as graphene having low specific gravity and high thermal conductivity have attracted attention.

Particularly, since the carbon nanotube has high thermal conductivity of about 2000 W/mK, although it may be greatly applicable as a nanofluid, it is limited to be used as a nanofluid filler because of surface hydrophobicity, low dispersion, and low suspension stability thereof.

Graphene as a carbon-based filler is formed of a monomer of carbon, and has excellent electrical, thermal, and mechanical characteristics, and particularly, its thermal conductivity is greater than about 3000 W/mK, having better thermal conductivity than the carbon nanotube. However, the grapheme has a stable two-dimensional planar structure in which hexagonal carbon structures are connected, thus it has no affinity with a solvent such as water and ethylene glycol for cooling.

Thus, in order to improve dispersion in the fluid, a graphene oxide having affinity with a polar solvent may be used. The graphene oxide may be selected as a nanofluid material due to greater dispersion than the graphene, for example, since various functional groups are applied on its surface. An epoxy (COC) group and a hydroxyl (OH) group exist in a fault plane of the graphene oxide, and a carboxyl (COOH) group and the like exist in an edge of the graphene. Those functional groups have polarity, thus they are well mixed with a generally used fluid such as water and ethylene glycol.

However, even though the graphene oxide has the high thermal conductivity, an actually used nanofluid flows through a tube used as a passage, and most of the tubes in which a fluid of a high temperature and a fluid of low temperature flow are made of a metal material. For a vehicle, for example, there are various kinds of metal materials such as aluminum, iron, steel, brass, and copper at the inside through which the antifreeze of the vehicle passes. However, most of the carbon materials may cause galvanic corrosion with these metal materials.

The galvanic corrosion occurs when two different metals are coupled and placed in a corrosion solution, and one metal is first corroded whereas the other metal is protected from the corrosion.

The galvanic corrosion may occur greater as a difference between anodic indexes as inherent potential values of the metals becomes greater. The graphite comprising carbons can be included in the highest cathode compared to a general metal. That is, when the graphite is with another metal, the graphite itself is reduced and oxidizes metals around it.

In order to overcome these drawbacks of the metal corrosion and to maintain the excellent thermal conductivity and dispersion stability of the graphene oxide, direct contact between the graphene oxide and the metal may be minimized, thermal conductivity may be maintained, and a dispersion process may be stably performed.

The above information disclosed in this Background section is only for enhancement of understanding of the background of the invention and therefore it may contain information that does not form the prior art that is already known in this country to a person of ordinary skill in the art.

SUMMARY OF THE INVENTION

In preferred aspects, the present invention provides a composite comprising a graphene oxide and a nanodiamond having improved dispersion stability and corrosion stability, and a manufacturing method thereof.

In addition, the present invention provides a nanofluid comprising the graphene oxide-nanodiamond composite having improved dispersion stability and corrosion stability.

The term "graphite oxide" as used herein refers to a compound comprising carbon, oxygen, and hydrogen in suitable ratios, and the graphite oxide may include carbon as main component constituting greater than about 50 wt %, greater than about 60 wt %, greater than about 70 wt %, greater than about 80 wt %, greater than about 90 wt %, greater than about 95 wt %, or greater than about 99 wt % of the total weight of the graphite oxide. The graphene oxide may be obtained by oxidizing graphene (a carbon material suitably in the form of a single, planar, two-dimensional, and honey-comb like lattice). The graphene oxide may include functional groups containing oxygen, such as epoxy, hydroxyl, or carboxyl groups.

The term "nanodiamond" as used herein refers to a diamond or a particle thereof having a size in nanometer scale, for example, having a size (e.g. cross-sectional dimension) less than about 999 nm, less than about 900 nm, less than about 800 nm, less than about, less than about 700 nm, less than about 600 nm, less than about 500 nm, less than about 400 nm, less than about 300 nm, less than about 200 nm, less than about 100 nm, or less than about 50 nm. The nanodiamond is not particularly limited in its shape, color, grade, composition, chemical modification formed thereon, or the like. In addition, the nanodiamond may include carbon as a main component constituting, for example, greater than about 50 wt %, greater than about 60 wt %, greater than about 70 wt %, greater than about 80 wt %, greater than about 90 wt %, greater than about 95 wt %, or greater than about 99 wt % of the total weight thereof. An exemplary embodiment of the present invention provides a composite comprising a graphene oxide and a nanodiamond. In particular, the nanodiamond may be bonded or attached on a surface of the graphene oxide. For instance, the nanodiamond may be chemically bonded on the surface of the graphene oxide.

The term "bonding" as used herein refers to attaching a substance to other, by chemical or physical means. Preferably, the bonding formed between the graphene oxide and the nanodiamond may be a chemical bond including a covalent bond or ionic bond, preferably covalent bond formed by chemical reaction.

The graphene oxide and the nanodiamond may be chemically bonded by a linker group. The linker group may be selected from the group consisting of an alkylene, a cycloalkylene, a bivalent aromatic ring group, —CO—O—, —S—, —O—, —CO—, —SO$_2$—, —N(R)— wherein R is a hydrogen atom or an alkyl group), and a combination thereof.

Preferably, the graphene oxide and the nanodiamond may be chemically bonded by —CO—O—.

Preferably, a thickness of the graphene oxide suitably may be about 1 to 2 nm, and a diameter thereof may be about 1 to 3 μm.

Preferably, an average diameter of the nanodiamond suitably may be about 3 to 10 nm.

Preferably, an amount of about 50 to 150 parts by weight of the nanodiamond based on 100 parts by weight of the graphene oxide may be chemically bonded to the graphene oxide.

Another exemplary embodiment of the present invention provides a method of manufacturing a composite comprising a graphene oxide and a nanodiamond. The method may comprise steps of: preparing a nanodiamond; attaching a functional group on a surface of the nanodiamond by heat-treating the nanodiamond; dispersing the nanodiamond comprising the functional group in a first solvent to prepare a nanodiamond dispersion; dispersing a graphene oxide in a second solvent to prepare a graphene oxide solution; mixing the graphene oxide dispersion and the nanodiamond dispersion; and forming a bond between the graphene oxide and the nanodiamond.

In the preparing of the nanodiamond, an average diameter of the nanodiamond suitably may be about 3 to 10 nm.

The functional group suitably may be attached on the surface of the nanodiamond by heat-treating the nanodiamond at a temperature of about 400° C. to 500° C. for about 1 to 3 hours.

Preferably, the functional group attached on the surface of the nanodiamond by the heat-treating the nanodiamond may be —COOH.

The nanodiamond dispersion may further comprise a catalyst. The catalyst suitably may be a nitrogen containing material, such as one or more selected from the group consisting of N,N'-dicyclohexylcarbodiimide (DCC) and 4-(dimethyl amino)pyridine (DMAP).

The nanodiamond comprising the functional group may be suitably dispersed in the first solvent, and the first solvent suitably may be one or more selected from the group consisting of an amide-based solvent, an ether-based solvent, and a halogenated solvent.

When the graphene oxide is dispersed in the second solvent, a hydroxyl group or an alkyl group may be attached on the surface of the graphene oxide.

Preferably, a thickness of the graphene oxide may be about 1 to 2 nm, and a diameter thereof may be about 1 to 3 μm.

An amount of about 50 to 150 parts by weight of the nanodiamond based on 100 parts by weight of the graphene oxide may be mixed with the graphene oxide to form a bond therebetween.

The bond between the graphene oxide and the nanodiamond may be formed by an esterification reaction.

Yet another embodiment of the present invention provides a nanofluid comprising the composite comprising a graphene oxide and a nanodiamond as described herein and a polar fluid.

The term "nanofluid" as used herein refers to a fluid that may contain particles having a size in nanometer scale, such as nanodiamond particles, graphene-oxide, or the composite formed of those particles. The nanofluid may also contain a fluid, particularly a liquid fluid (matrix) suitably.

The polar fluid suitably may be selected from the group consisting of water, ethylene glycol, propylene glycol, or a combination thereof.

Further provided is a vehicle that may comprise the nanofluid as described herein.

Other aspects of the invention are disclosed infra.

The graphene oxide-nanodiamond composite according to the exemplary embodiment of the present invention may be used as a nanomaterial to produce a nanofluid which satisfies dispersion stability and metal corrosion stability and which has substantially improved thermal conductivity.

The composite according to the exemplary embodiment of the present invention may change a planar structure of graphene into a three-dimensional structure to limit contact (caused by steric hindrance) among plane graphene, thus nanodiamond particles may be bonded to a wide surface of graphene to increase resistance to precipitation in a fluid to be stably dispersed.

The nanofluid according to the exemplary embodiment of the present invention may provide high thermal conductivity, thus it may be applied to a vehicle and a thermal management system, and to various apparatuses and systems which require a fluid having excellent thermal conductivity.

BRIEF DESCRIPTION OF THE DRAWINGS

It should be understood that the accompanying drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment. In the figures, reference numbers refer to the same or equivalent parts of the present invention throughout the several figures of the drawing.

DETAILED DESCRIPTION

The advantages and features of the present invention and the methods for accomplishing the same will be apparent from the exemplary embodiments described hereinafter with reference to the accompanying drawings. However, the present invention is not limited to the exemplary embodiments described hereinafter, but may be embodied in many different forms. The following exemplary embodiments are provided to make the invention of the present invention complete and to allow those skilled in the art to clearly understand the scope of the present invention, and the present invention is defined only by the scope of the appended claims. Throughout the specification, the same reference numerals denote same constituent elements.

In some exemplary embodiments, detailed description of well-known technologies will be omitted to prevent the invention of the present invention from being interpreted ambiguously. Unless otherwise defined, all terms (including technical and scientific terms) used herein have the same meaning as commonly understood by one of ordinary skill in the art. In addition, throughout the specification, unless explicitly described to the contrary, the word "comprise" and variations such as "comprises" or "comprising" will be understood to imply the inclusion of stated elements but not the exclusion of any other elements. Further, as used herein, the singular forms "a", "an", and "the" are intended to include the plural forms as well, unless the context clearly indicates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

Throughout the specification, unless otherwise defined, "average diameter" refers to an average of the longest diameter of each particle in the group.

As used herein, unless otherwise defined, "substituted" refers to a group substituted with a C1 to C30 alkyl group, a C1 to C10 alkylsilyl group, a C3 to C30 cycloalkyl group, a C6 to C30 aryl group, a C2 to C30 heteroaryl group, a C1 to C10 alkoxy group, a fluoro group, a C1 to C10 trifluoroalkyl group such as trifluoromethyl group, or a cyano group.

As used herein, unless otherwise defined, "alky group" includes "saturated alkyl group" having no alkene or alkyne group, or "unsaturated alkyl group" having at least one alkene or alkyne group. The "alkene group" means a substituent having at least two carbon atoms bound to each other via at least one carbon-carbon double bond, and "alkyne group" means a substituent having at least two carbon atoms bound to each other via at least one carbon-carbon triple bond. The alkyl group may be branched, linear, or cyclic.

The alkyl group may be a C1 to C20 alkyl group, more particularly a C1 to C6 lower alkyl group, a C7 to C10 medium alkyl group, or a C11 to C20 higher alkyl group.

For example, a C1 to C4 alkyl group means an alkyl group having 1 to 4 carbon atoms in its alkyl chain, and is selected from the group consisting of methyl, ethyl, propyl, isopropyl, n-butyl, isobutyl, sec-butyl, and tert-butyl.

Typical alkyl groups include methyl, ethyl, propyl, isopropyl, butyl, isobutyl, tert-butyl, pentyl, hexyl, ethenyl, propenyl, butenyl, cyclopropyl, cyclobutyl, cyclopentyl, cyclohexyl, or the like.

According to an exemplary embodiment of the present invention, a graphene oxide-nanodiamond complex includes a graphene oxide and a nanodiamond attached on the surface of the graphene oxide. For example, the graphene oxide and the nanodiamond may be chemically bonded, for example, by a covalent bond, ionic bond, or the like.

According to an exemplary embodiment of the present invention, provided is a composite of including the graphene oxide and the nanodiamond complex, which may be chemically bonded nanomaterials. The graphene oxide may have high dispersion in a polar solution and high thermal conductivity but low corrosion stability, and the nanodiamond may have high metal corrosion stability and high thermal conductivity but low dispersion to a polar solution. According to an exemplary embodiment of the present invention, the composite comprising the graphene oxide and nanodiamond may be used as a nanomaterial to manufacture a nanofluid which satisfies both dispersion stability and metal corrosion stability and has high thermal conductivity.

Generally, a nanodiamond, as used herein, may be formed by an explosive reaction of graphite, and may be formed in fine nanoparticles. The nanodiamond generally may contain various functional groups on the surface thereof, unlike a general diamond.

Generally, the nanodiamond does not have a complete $SP^3$ structure and may include various functional groups. Particularly, functional groups may become various depending on conditions of an explosive reaction. For example, the surface of the nanodiamond may have a functional group such as alkyl, cycloalkyl, alkenyl, —COOH, —SH, —OH, —COH, and —SO$_2$H—N(R)H (R is a hydrogen atom or an alkyl group). However, for a selective chemical reaction, one functional group among surface reaction groups may be modified to be predominant, and the nanodiamond and the graphene oxide may be chemically bonded through the functional group and the chemical reaction with the functional group formed on the surface of the graphene oxide.

Particularly, the graphene oxide and the nanodiamond may be chemically bonded through an alkylene group, a cycloalkylene group, a bivalent aromatic ring group, —CO—O, —S—, —O—, —CO—, —SO$_2$—, —N(R)— (R is a hydrogen atom or a alkyl group), and a bivalent linking group which is a complex thereof. More particularly, the graphene oxide and the nanodiamond may be chemically bonded through —CO—O—.

Figure 1:
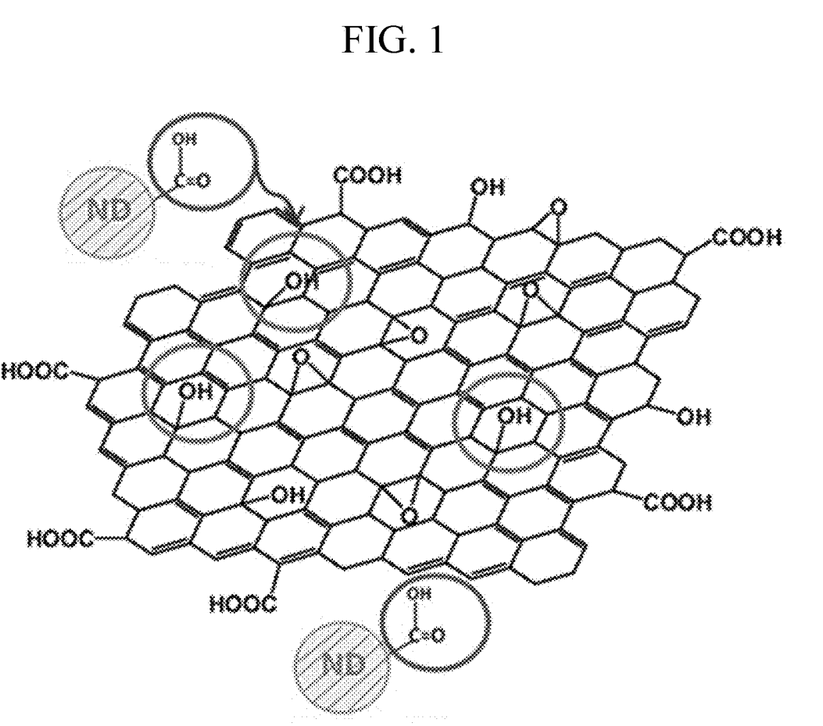
FIG. 1 illustrates an exemplary composite of a graphene oxide and a nanodiamond according to an exemplary embodiment of the present invention.

FIG. 1 illustrates an exemplary graphene oxide-nanodiamond complex according to an exemplary embodiment of the present invention. As shown in FIG. 1, a chemical bond by —CO—O— may be formed by an esterification reaction of a —COOH functional group introduced on a surface of a nanodiamond and an —OH functional group introduced on a surface of a graphene oxide. However, the present invention is not limited thereto, and it may be bonded through various bivalent linking groups.

Since a graphene oxide (GO) has a planar structure, it may provide sufficient space for attaching the nanodiamond, which may be a circular-shaped particle. The graphene oxide may have a nanosize in a thickness direction, while it is a plane spread by a length of a micrometer size, thus the graphene oxide may have a surface reaction with several nanodiamonds. In other words, the several nanodiamonds may approach into a surface reaction with the graphene oxide and may cover a surface of the graphene oxide. When the nanodiamonds are bonded to a top surface and a bottom surface of the graphene oxide, an actual metal may not be directly bonded to the surface of the graphene oxide, and the nanodiamond may contact a surface of the metal. As a result, a metal corrosion problem by the graphene oxide may be solved. Moreover, the nanodiamond with high thermal conductivity may be attached or bonded on the graphene oxide, thus a decrease of the thermal conductivity may not occur, and aggregation between the graphene oxides may decrease due to the nanodiamond bonded on the surface of the graphene oxide.

Although the graphene oxide may be highly dispersed in a polar solvent, contact between graphenes may be applied to produce steric hindrance due to the nanodiamond, thereby increasing dispersion stability for a long period.

A thickness of the graphene oxide may be about 1 to 2 nm, and a diameter of the graphene oxide may be about 1 to 3 µm. According to the thickness and diameter, sufficient space in which the nanodiamonds may be bonded is provided.

An amount of about 50 to 150 parts by weight of the nanodiamond based on 100 parts by weight of the graphene oxide may be chemically bonded to the graphene oxide. In other words, a weight ratio between the nanodiamond and the graphene oxide to form suitable bonding may be about 0.5-1.5:1 by weight. When the bonded amount of the nanodiamond is less than the predetermined amount, for example, less than about 50 parts by weight based on 100 parts by weight of the graphene oxide, the metal corrosion stability may deteriorate. In contrast, when the bonded amount of the nanodiamond is greater than the predetermined amount, for example, greater than about 150 parts by weight based on 100 parts by weight of the graphene oxide, the dispersion stability may deteriorate.

Figure 2:
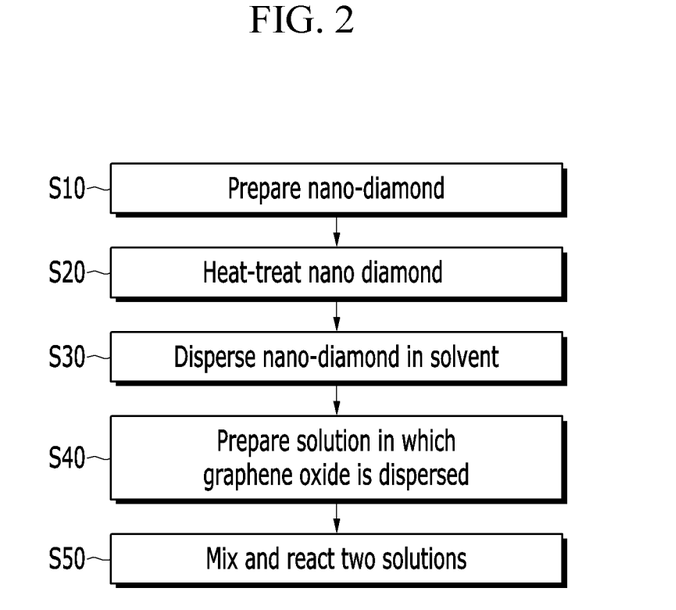
FIG. 2 illustrates an exemplary manufacturing method of an exemplary composite comprising a graphene oxide and a nanodiamond according to an exemplary embodiment of the present invention.

FIG. 2 illustrates a flowchart of a manufacturing method of a graphene oxide-nanodiamond complex according to an exemplary embodiment of the present invention, however, and the present invention is not limited thereto. Thus, a manufacturing method of the graphene oxide-nanodiamond complex may be variously modified.

As shown in FIG. 2, the manufacturing method of the graphene oxide-nanodiamond according to the exemplary embodiment of the present invention may include: preparing a nanodiamond at step S10; attaching a functional group on a surface of the nanodiamond by heat-treating the nanodiamond at step S20; dispersing the nanodiamond comprising the functional group in a first solvent at step S30 thereby forming a nanodiamond dispersion; dispersing a graphene oxide in a second solvent thereby forming a graphene oxide dispersion at step S40; mixing the graphite oxide solution with the nanodiamond dispersion; and forming a bond reaction at step S50.

Respective steps will be described in detail.

First, the nanodiamond may be prepared at step S10. Since the nanodiamond has been described above, a duplicated description thereof will be omitted.

Next, the functional group is introduced on the surface by heat-treating the nanodiamond at step S20. For a selective chemical reaction, at least one functional group among surface reaction groups present in the nanodiamond may be modified to be predominant. When the heat treatment is performed by one method described above, some unstable functional groups on the surface of the nanodiamond may be oxidized and changed to a carboxyl (—COOH) group. For example, the heat treatment may be performed for about 1 to 3 hours at a temperature of about 400° C. to 500° C. in the air.

When the heat treatment temperature is less than the predetermined range, for example, less than about 400° C., the functional group may not be sufficiently introduced, and when the heat treatment temperature is greater than the predetermined range, for example, greater than about 500° C., the nanodiamond may be carbonized. When the reaction time is less than the predetermined range, for example, less than about 1 hour, a reaction may not be sufficiently performed, and when the reaction time is greater than the predetermined range, for example, greater than about 3 hour, the nanodiamond may be carbonized.

The nanodiamond treated by heat and containing the predominant functional group may be dispersed in the first solvent at step S30. In this case, a catalyst may be added to the nanodiamond dispersion for promoting a bond formation reaction with the graphene oxide. For example, the catalyst may be one or more selected from the group consisting of N,N'-dicyclohexylcarbodiimide (DCC) and 4-(dimethyl amino)pyridine (DMAP).

For example, when the DCC is used as catalyst, the —COOH functional group formed on the surface of the nanodiamond may be activated according to Reaction Formula 1, and may react with the graphene oxide. Accordingly, the nanodiamond and the graphene oxide may form chemically bonding through the —CO—O— group.

[Reaction Formula 1]

The solvent is not limited as long as it properly disperses the nanodiamond, and it may be one or more selected from the group consisting of an amide-based solvent, an ether-based solvent, and a halogenated solvent. Preferably, the amide solvent may include dimethylformamide (DMF), dimethylacetamide (DMAc), and N-methyl-2-pyrrolidone (NMP). The ether-based solvent suitably may include tetrahydrofuran (THF) and dioxane. The halogenated solvent suitably may be chloroform or methylene chloride.

The graphene oxide dispersion in which the graphene oxide is dispersed in the second solvent is manufactured at step S40. A description with respect to the graphene oxide is the same as the above-mentioned description, so a repeated description thereof will be omitted. A hydroxyl group or an alkyl group may be attached on the surface of the graphene oxide at step S40.

Next, the graphene oxide dispersion may be mixed with the nanodiamond dispersion and the graphene oxide and the nanodiamond may be bonded at step S50.

Preferably, an amount of about 50 to 150 parts by weight of the nanodiamonds based on 100 parts by weight of the graphene oxide may be bonded, by a chemical bonding such as covalent bond, with the graphene oxide. When the bonded amount of the nanodiamond is less than the predetermined amount, for example, less than about 50 parts by weight based on 100 parts by weight of the graphene oxide, the metal corrosion stability may deteriorate. In contrast, when the bonded amount of the nanodiamond is greater than the predetermined amount, for example, greater than about 150 parts by weight based on 100 parts by weight of the graphene oxide, the dispersion stability may deteriorate.

The bond may be formed by an esterification reaction forming ester bond according to Reaction Formula 1. Other reactions may occur between functional groups in the graphene oxide and the nanodiamond.

In addition, according to the exemplary embodiment of the present invention, the nanofluid may include the above described compositing comprising the graphene oxide and the nanodiamond and the polar fluid.

According to the nanofluid including the graphene oxide-nanodiamond complex, since the corrosion stability to the metal through which the fluid flows may be achieved, the aggregation among the nanoparticles may be prevented, and two materials having high thermal conductivity are bonded, the characteristic deterioration problem may be solved.

The polar fluid suitably may be selected from the group consisting of water, ethylene glycol, propylene glycol, and a combination thereof.

The nanofluid may be manufactured by mixing and dispersing the nanodiamond and the polar fluid.

EXAMPLE

Hereinafter, examples of the present invention and comparative examples are described. These examples, however, should not in any sense be interpreted as limiting the scope of the present invention.

Figure 3:
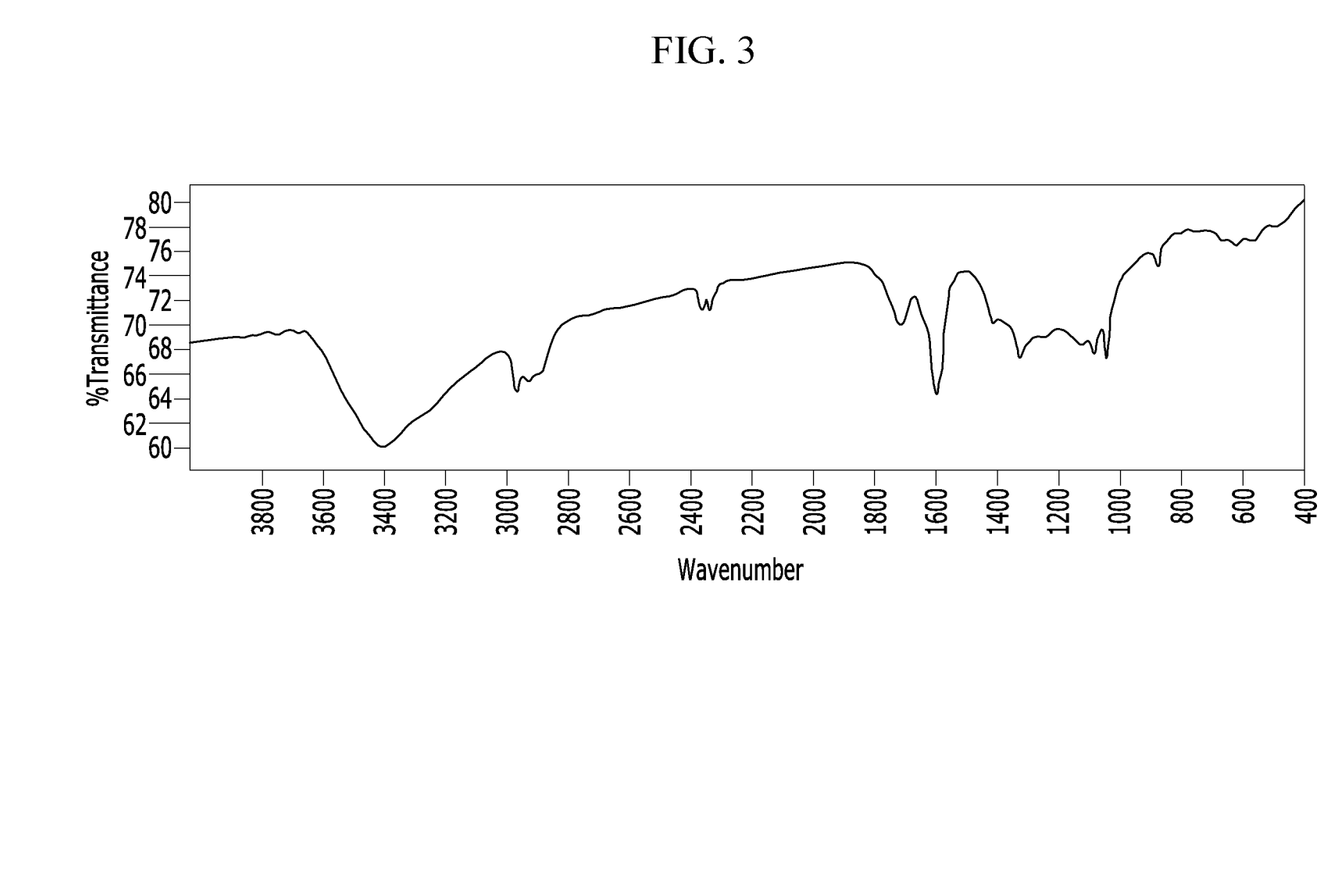
FIG. 3 illustrates a result of infrared spectroscopic analysis (FT-IR) of an exemplary nanodiamond before heat treatment in an exemplary embodiment of the present invention.
Figure 4:
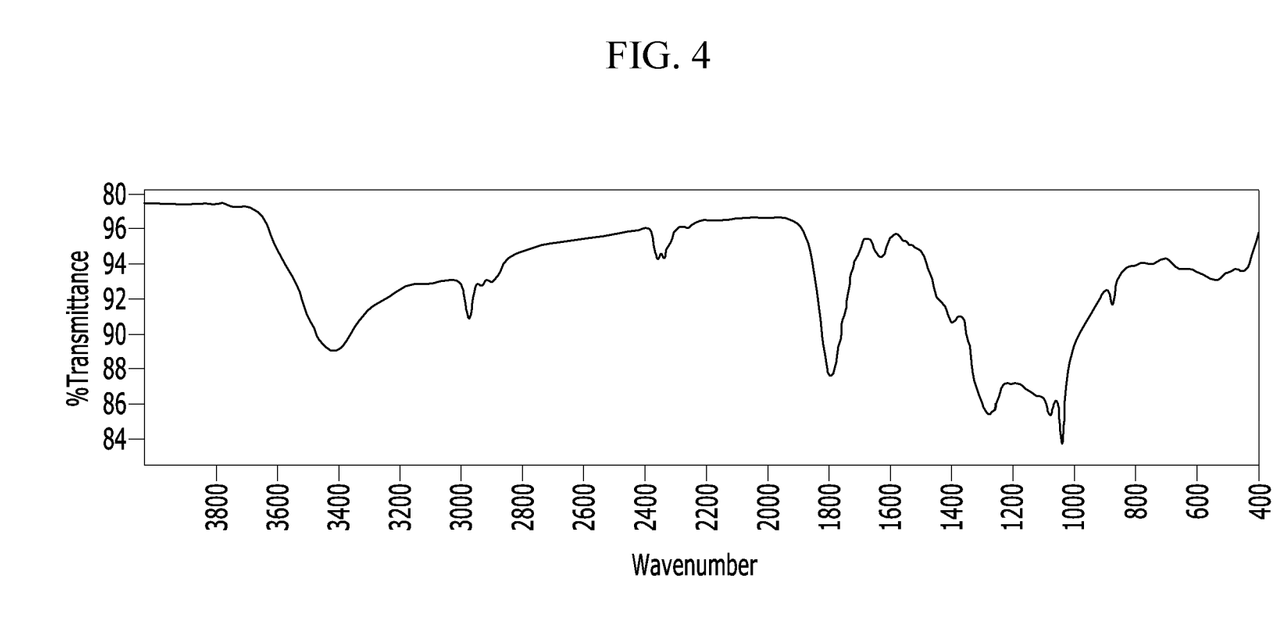
FIG. 4 illustrates a result of infrared spectroscopic analysis (FT-IR) of an exemplary nanodiamond after heat treatment in an exemplary embodiment of the present invention.

Exemplary Embodiment: Preparation of the Graphene Oxide-Nanodiamond Complex 0.1 g of the nanodiamond (Manufacturer: HeYuan ZhongLian Nanotech Co. LTD) was prepared by pulverizing with jet mill until obtaining an average diameter of about 20 nm. The nanodiamond powder was heat-treated for about 1 h at 500° C. in the air. FIG. 3 and FIG. 4 illustrate the infrared spectroscopic analysis result of the nanodiamond before and after the heat treatment, respectively. As shown in FIG. 4, a peak was observed around about 1764 cm$^{-1}$, and it can be confirmed that a C=O functional group of COOH was formed.

The heat-treated nanodiamond was introduced into 100 ml of tetrahydrofuran (THF) and dispersed by ultrasonic waves for about 2 h, 5 g of N,N'-dicyclohexylcarbodiimide (DCC) was introduced into 50 ml of a tetrahydrofuran (THF) solution, then the DCC solution was introduced into and mixed with the nanodiamond dispersion solution.

0.1 g of the graphene oxide (thickness of 1 nm and diameter of 2 μm) was introduced into the THF solution and dispersed by ultrasonic waves for about 2 h, the nanodiamond was added to the DCC complex solution, and then the esterification bond reaction was performed for about 12 h.

After the reaction, a resulting sediment was filtered, washed, and dried to obtain the graphene oxide-nanodiamond complex.

Figure 5:
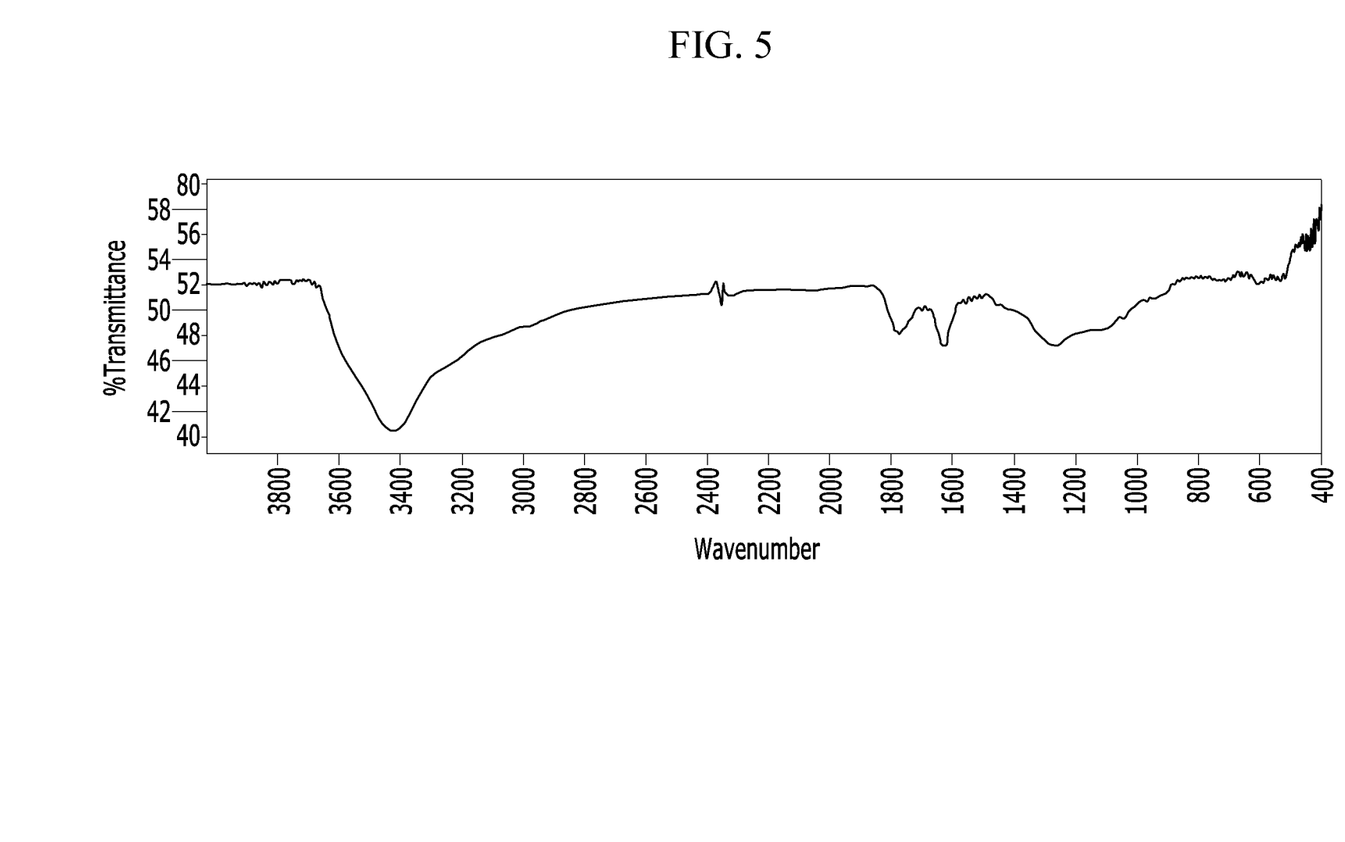
FIG. 5 illustrates an infrared spectroscopic analysis (FT-IR) result of an exemplary composite comprising a graphene oxide and a nanodiamond manufactured according to an exemplary embodiment of the present invention.

FIG. 5 illustrates infrared spectroscopic analysis results of the prepared graphene oxide-nanodiamond complex. As shown in FIG. 5, it can be confirmed that the C=O peak was weakened and the chemical bond between the graphene oxide and the nanodiamond was formed.

Figure 6:
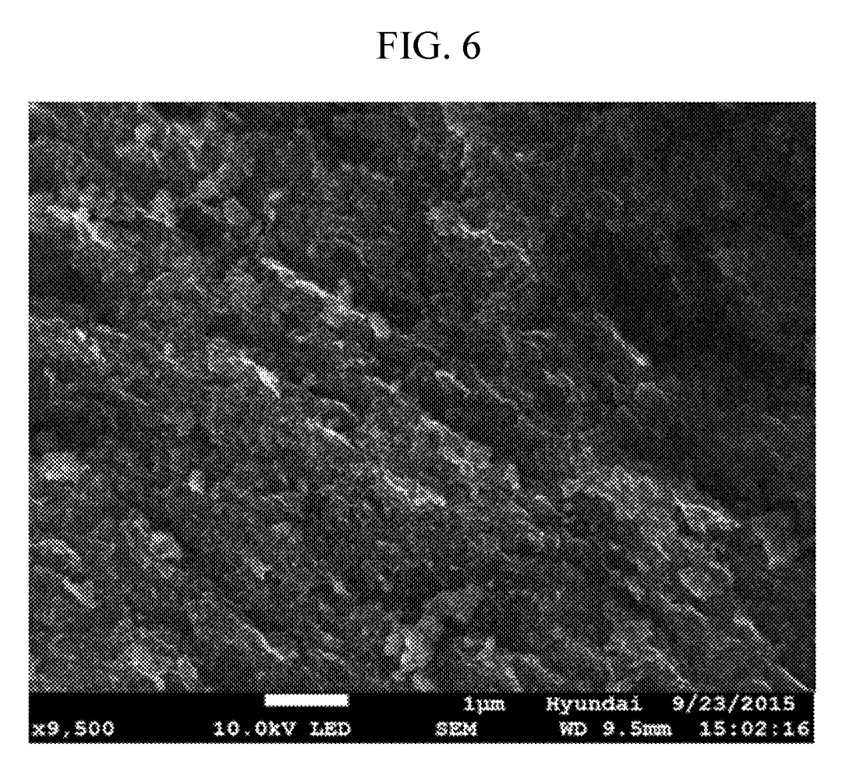
FIG. 6 illustrates a scanning electron microscope (SEM) photograph of an exemplary composite comprising a graphene oxide and a nanodiamond manufactured according to an exemplary embodiment of the present invention.

FIG. 6 illustrates a scanning electron microscope (SEM) photograph of the prepared graphene oxide-nanodiamond complex. As shown in FIG. 6, it can be confirmed that the nanodiamond particles were bonded on the planar graphene.

Experimental Example

Preparation and Evaluation of the Nanofluid 5 parts by weight of the graphene oxide-nanodiamond complex prepared according to the exemplary embodiment were added to 95 parts by weight of a 1:1 complex solvent of water and ethylene glycol, and were dispersed by ultrasonic waves to prepare the nanofluid.

Figure 7:
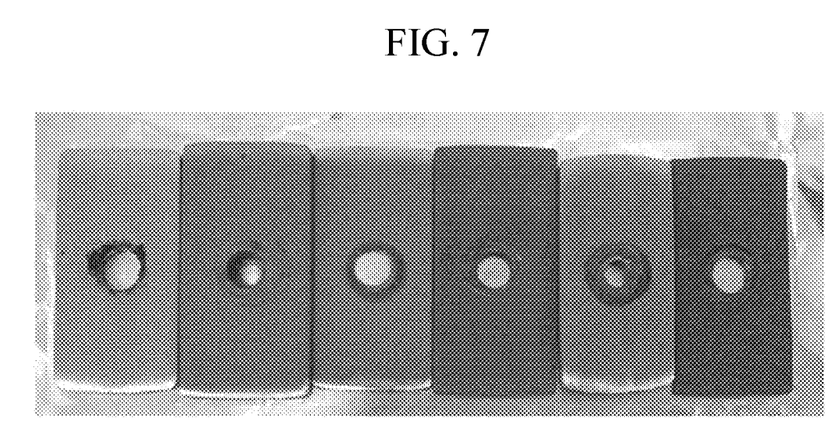
FIG. 7 illustrates a metal corrosion test result for an exemplary nanofluid in an experimental example according to an exemplary embodiment of the present invention.

In order to test the metal corrosion of the nanofluid, aluminum, cast iron, steel, brass, solder, and copper as samples were prepared, and were dipped into the nanofluid. FIG. 7 illustrates a photograph of the metal samples after being taken out.

Table 1 represents the corrosion states of the metal samples observed by the naked eye.

Figure 8:
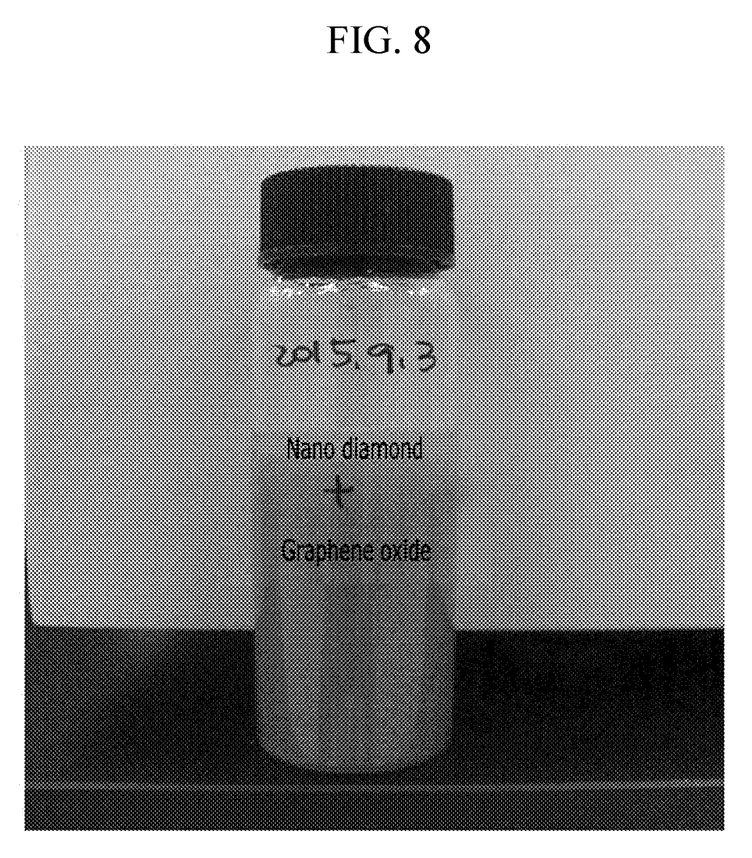
FIG. 8 illustrates a photograph of an exemplary nanofluid manufactured in an experimental example according to an exemplary embodiment of the present invention.

FIG. 8 illustrates a photograph after the prepared nanofluid is left to stand. As shown in FIG. 8, it can be seen that the dispersion was excellent even though the prepared nanofluid was left to stand for a long period of time.

Comparative Example

The nanofluid was prepared by adding the graphene oxide to 95 parts by weight of a 1:1 complex solvent of water and ethylene glycol and dispersing them with ultrasonic waves.

Figure 9:
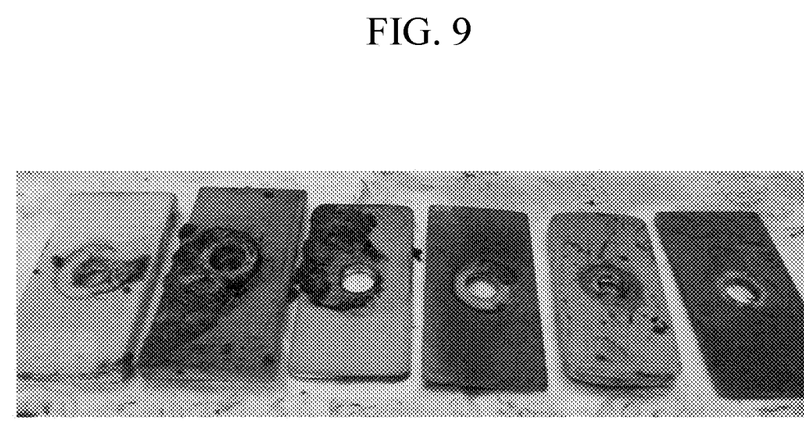
FIG. 9 illustrates a metal corrosion test result of a nanofluid in a comparative example.

The same corrosion test as in the experimental example described above was performed, and a photograph of the metal samples which were taken out was illustrated in FIG. 9.

Table 1 represents the corrosion states of the metal samples observed with the naked eye.

TABLE 1

|  | Aluminum | Cast iron | Steel | Brass | Solder | Copper |
| --- | --- | --- | --- | --- | --- | --- |
| Experimental Example | No corrosion | No corrosion | No corrosion | No corrosion | No corrosion | No corrosion |
| Comparative Example | Severe corrosion | Severe corrosion | Severe corrosion | Severe corrosion | Severe corrosion | Severe corrosion |

As represented in Table 1, it can be seen that the nanofluid including the graphene oxide-nanodiamond complex according to the exemplary embodiment of the present invention had excellence corrosion stability.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the embodiments described above are only examples and should not be construed as being limitative in any respects.

What is claimed is:

1. A method of manufacturing a composite comprising a graphene oxide and a nanodiamond, comprising:
   preparing a nanodiamond;
   attaching a functional group on a surface of the nanodiamond by heat-treating the nanodiamond;
   dispersing the nanodiamond comprising the functional group in a first solvent to prepare a nanodiamond dispersion;
   dispersing a graphene oxide in a second solvent to prepare a graphene oxide dispersion; and
   mixing the graphene oxide dispersion and the nanodiamond dispersion; and
   forming a bond between the graphene oxide and the nanodiamond,
   wherein the nanodiamond dispersion further comprises a catalyst.

2. The method of claim 1, wherein an average diameter of the nanodiamond is about 3 to 10 nm.

3. The method of claim 1, wherein
   the functional group is attached on the surface of the nanodiamond by heat-treating the nanodiamond at a temperature of about 400° C. to 500° C. for about 1 to 3 h.

4. The method of claim 1, wherein the functional group attached on the surface of the nanodiamond is —COOH.

5. The method of claim 1, wherein the catalyst is one or more selected from the group consisting of N,N'-dicyclohexylcarbodiimide (DCC) and 4-(dimethyl amino)pyridine (DMAP).

6. The method of claim 1, wherein the first solvent is one or more selected from the group consisting of an amide-based solvent, an ether-based solvent, and a halogenated solvent.

7. The method of claim 1, wherein when the graphene oxide is dispersed in the second solvent, a hydroxyl group or an alkyl group is attached on the surface of the graphene oxide.

8. The method of claim 1, wherein when the graphene oxide is dispersed in the second solvent, a thickness of the graphene oxide is about 1 to 2 nm, and a diameter thereof is about 1 to 3 μm.

9. The method of claim 1, wherein an amount of about 50 to 150 parts by weight of the nanodiamond based on 100 parts by weight of the graphene oxide are mixed with the graphene oxide to form the bond between the graphene oxide and the nanodiamond.

10. The method of claim 1, wherein the bond between the graphene oxide and the nanodiamond is formed by esterification reaction.

\* \* \* \* \*